United States Patent
Caringi et al.

(12)

(10) Patent No.: US 6,570,038 B1
(45) Date of Patent: May 27, 2003

(54) AQUEOUS HEXASUBSTITUTED GUANIDINIUM CHLORIDES AND METHODS FOR THEIR PREPARATION AND USE

(76) Inventors: Joseph John Caringi, 2 Nicholas Ave., Niskayuna, NY (US) 12309; Peter David Phelps, 142 Gordon Rd., Schenectady, NY (US) 12306; Thomas Link Guggenheim, 3401 Upton Rd., Mt. Vernon, IN (US) 47620; Daniel Joseph Brunelle, 4 Woods Edge, Burnt Hill, NY (US) 12027

( * ) Notice: Subject to any disclaimer, the term of this patent is extended or adjusted under 35 U.S.C. 154(b) by 117 days.

(21) Appl. No.: 09/591,426

(22) Filed: Jun. 9, 2000

Related U.S. Application Data

(62) Division of application No. 09/216,252, filed on Dec. 17, 1998, now Pat. No. 6,235,934, which is a division of application No. 08/583,921, filed on Jan. 11, 1996, now Pat. No. 5,872,294.

(51) Int. Cl.[7] .............................................. C07C 279/02
(52) U.S. Cl. ........................ 564/241; 564/230; 564/237; 564/240; 564/57; 564/61; 548/473; 548/485; 546/186; 546/245
(58) Field of Search ........................... 564/240, 57, 61, 564/230; 546/186, 245

(56) References Cited

U.S. PATENT DOCUMENTS

| 5,132,423 A | * | 7/1992 | Brunelle et al. | ............. 544/162 |
| 5,759,406 A | * | 6/1998 | Phelps et al. | ............... 210/673 |

* cited by examiner

*Primary Examiner*—Shailendra Kumar

(57) ABSTRACT

Hexasubstituted guanidinium chlorides are prepared by a method which affords them in high yield as aqueous solutions, optionally also containing alkali metal chlorides. The solutions may be employed as sources of hexasubstituted guanidinium salts useful as phase transfer catalysts for the reaction of alkali metal salts of dihydroxyaromatic compounds with substituted imides to form polyetherimides or their intermediates.

22 Claims, No Drawings

AQUEOUS HEXASUBSTITUTED GUANIDINIUM CHLORIDES AND METHODS FOR THEIR PREPARATION AND USE

This application is a division of application Ser. No. 09/216,252, filed Dec. 17, 1998 now U.S. Pat. No. 6,235,934 which is a division of application Ser. No. 08/583,921 filed on Jan. 11, 1996, now U.S. Pat. No. 5,872,294 which is hereby incorporated by reference in its entirety.

BACKGROUND OF THE INVENTION

This invention relates to phase transfer catalysis. More particularly, it relates to the preparation of aqueous solutions of hexasubstituted guanidinium salts useful as phase transfer catalysts, and to the use of such solutions in the preparation of polyetherimides and intermediates therefor.

The use of hexaalkylguanidinium salts as phase transfer catalysts in various reactions is known. Many of these reactions are characterized by the necessity of conducting them under anhydrous conditions. This makes it very difficult to introduce measured amounts of the hexasubstituted guanidinium salt into the reaction mixture, since such salts are solids and are only sparingly soluble in the organic solvents employed.

Hexasubstituted guanidinium salts may be prepared by a series of three reactions: the phosgenation of a secondary amine to produce a tetrasubstituted urea; further phosgenation of the tetrasubstituted urea to form a chloroformamidinium chloride, also known as a "Vilsmeier salts" and sometimes designated as such hereinafter; and finally, the reaction of the Vilsmeier salt with further secondary amine to produce the hexasubstituted guanidinium chloride. The third of these reactions must be conducted under anhydrous conditions, and the second is preferably anhydrous also.

It is frequently found that preparation of the Vilsmeier salt in good yield cannot be achieved unless expensive solvents such as acetonitrile are employed or a substantial excess of phosgene is used. This is true, for example, of the method described in Kantlehner et al., *Liebigs Ann. Chem.*, 1984, 108–126, which afforded the hexasubstituted guanidinium salt in 94% yield but employed acetonitrile as the solvent. A method employing phosphorus oxychloride in toluene is described in Example 1 of U.S. Pat. No. 5,132,423; it afforded the product in 87% yield. A method employing phosgene and toluene, described in Barton et al., *J. Chem. Soc., Perkin Trans.*, 1982, 2085–2090, resulted in a relatively low yield (85%) even with the use of a substantial excess of phosgene (molar ratio 1.95:1). The use of a large excess of phosgene, in any event, is undesirable since phosgene is toxic and is difficult to contain during the reaction. Moreover, disposal of a large excess of phosgene generally requires a sparging operation including passage through a caustic scrubber, presenting a potential hazardous waste problem upon disposal.

The product of the above-described series of reactions is invariably the hexasubstituted guanidinium chloride. It has further been found that the chlorides are hygroscopic, making their use under anhydrous conditions complicated. Therefore, they are often converted to other salts such as the bromides. This necessitates an additional reaction step, which is also expensive and therefore undesirable.

The use of hexasubstituted guanidinium salts as phase transfer catalysts in the reaction of bisphenol salts with halo- or nitro-substituted phthalimides to form bisimides, which are conventional intermediates for polyetherimide production, is described in Example 4 of U.S. Pat. No. 5,081,298. Its use in the direct preparation of polyetherimides by the reaction of bisphenol salts with similarly substituted bis(phthalimido) compounds is disclosed in U.S. Pat. No. 5,229,482. In each case, the guanidinium salts were added in solid form, which, as previously mentioned, presents numerous problems in commercial operations. Anhydrous conditions are mandatory in these reactions, since the presence of even traces of water can drastically decrease yields.

Methods of preparing hexasubstituted guanidinium salts in high yield and using them in a convenient manner as phase transfer catalysts in commercial operations, therefore, continue to be desirable subjects of investigation.

SUMMARY OF THE INVENTION

The present invention has numerous aspects relating to the preparation of hexasubstituted guanidinium salts and intermediates therefor, compositions comprising such salts and the use of such compositions as phase transfer catalysts in the preparation of polyetherimides and intermediates therefor. Each aspect is summarized immediately below.

First aspect: a method for preparing an aqueous solution of a hexasubstituted guanidinium salt which comprises the steps of:

(A) passing phosgene into a mixture comprising an aliphatic or alicyclic secondary amine, water and an organic solvent of low polarity at a reaction temperature in the range of about 40–80° C. and a pH in the range of about 10–13 maintained by the addition of an alkali metal base; the proportion of water being effective to produce a solution of by-product alkali metal chloride having a concentration of at least about 95% by weight of the saturation concentration under the prevailing reaction conditions, the ratio of equivalents of phosgene to said amine being in the range of 1.0–1.15:1, the volume ratio of organic solvent to water being in the range of about 0.8–5.0:1 and the proportion of amine being calculated to afford about a 25–90% by weight solution of product in said organic solvent assuming complete conversion, to produce a first product mixture comprising tetrasubstituted urea;

(B) removing water, amine and alkali metal chloride from said first product mixture to produce a first product mixture;

(C) adjusting said first product mixture to a tetrasubstituted urea concentration in the range of about 40–80% by weight by the addition or removal of organic solvent if necessary;

(D) introducing phosgene at a temperature in the range of about 60–80° C., the proportion of phosgene added being effective to react with any water present plus a ratio of equivalents of phosgene to said tetrasubstituted urea in the range of 1.05–1.15:1, to produce an anhydrous mixture comprising tetrasubstituted chloroformamidinium chloride;

(E) removing any unreacted phosgene from said anhydrous mixture;

(F) adding secondary amine to said anhydrous mixture in an amount effective to convert said tetrasubstituted chloroformamidinium chloride to hexasubstituted guanidinium salt; and (G) diluting said hexasubstituted guanidinium salt with water in a basic medium to produce aqueous and organic phases, removing said organic phase comprising unreacted secondary amine, and acidifying said aqueous phase containing said hexasubstituted guanidinium salt as necessary to adjust its pH to a value in the range of 2–12.

Second and third aspects: methods for preparing a tetrasubstituted urea which comprises step A, and for preparing a tetrasubstituted chloroformamidinium chloride which comprises steps D and E, all as defined above.

Fourth aspect: a method for preparing an aqueous solution of a hexasubstituted guanidinium salt having one or more chains containing at least 3 carbon atoms attached to each nitrogen atom which comprises the steps of:

(H) passing phosgene into a mixture comprising an aliphatic or alicyclic secondary amine, water and an organic solvent of low polarity at a reaction temperature in the range of about 40–80° C. and a pH in the range of about 10–13 maintained by the addition of an alkali metal base, to produce a first product mixture comprising tetrasubstituted urea;

(J) removing water, amine and alkali metal chloride from said first product mixture to produce a first product mixture;

(K) introducing phosgene at a temperature in the range of about 60—80° C. to produce an anhydrous mixture comprising tetrasubstituted chloroformamidinium chloride;

(L) removing any unreacted phosgene from said anhydrous mixture;

(M) adding secondary amine to said anhydrous mixture in an amount effective to convert said tetrasubstituted chloroformamidinium chloride to hexasubstituted guanidinium salt in a second product mixture;

(N) diluting said second product mixture with an amount of water in a basic medium, said amount of water being effective to cause the formation of three liquid phases, isolating the middle phase comprising said hexasubstituted guanidinium salt and acidifying said middle phase as necessary to adjust its pH to a value in the range of 2–12.

Fifth aspect: a composition comprising an aqueous solution of a hexasubstituted guanidinium chloride having a pH in the range of 2–12.

Sixth aspect: a composition comprising a hexasubstituted guanidinium chloride in aqueous solution and at least one of the following:

an imide having the formula

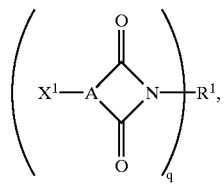

(I)

wherein A is a trivalent aromatic radical, $R^1$ is an unsubstituted or substituted mono- or divalent hydrocarbon radical containing about 1–13 carbon atoms, $X^1$ is halo or nitro and q is 1 or 2; and an alkali metal salt of a dihydroxyaromatic compound.

Seventh aspect: a method for preparing a polyetherimide or intermediate therefor which comprises the steps of:

(P) removing substantially all water from a mixture comprising an aqueous solution of a hexasubstituted guanidinium chloride to form an anhydrous mixture comprising said hexasubstituted guanidinium chloride;

(R) preparing, in an organic solvent of low polarity, an anhydrous mixture comprising said hexasubstituted guanidinium chloride; an imide having formula I and an alkali metal salt of a dihydroxyaromatic compound; and (S) effecting reaction in said anhydrous mixture between said alkali metal salt and said imide.

DETAILED DESCRIPTION; PREFERRED EMBODIMENTS

The hexasubstituted guanidinium (hereinafter sometimes simply "guanidinium" for brevity) chlorides which are the subject of the present invention include all those disclosed in the aforementioned U.S. Pat. No. 5,132,423, the disclosure of which is incorporated by reference herein. In preferred embodiments, the guanidinium chlorides have the formula

(II)

wherein $R^2$ is a $C_{1-6}$ primary alkyl radical or two $R^2$ values with the connecting nitrogen atom form a saturated heterocyclic radical. Such compounds may be prepared by the above-described three-step method wherein the secondary amine has the formula $(R^2)_2NH$.

The first aspect of the invention is chiefly effective for production of compositions comprising hexaethylguanidinium chloride, by reason of its solubility characteristics; however, the invention also contemplates its use for other guanidinium chlorides. In step A, phosgene is passed into a mixture of amine, water and an organic solvent of low polarity. Suitable organic solvents include aliphatic and aromatic hydrocarbons and halogenated aromatic hydrocarbons, as illustrated by benzene, toluene, xylene, chlorobenzene, o-dichlorobenzene, chlorotoluene, dichlorotoluene and octane. Aromatic solvents which form azeotropic mixtures with water are preferred; these include benzene, toluene and xylene. Thus, aromatic hydrocarbons are particularly preferred and toluene is most preferred.

The conditions of the reaction between phosgene and the secondary amine are critical for obtaining a high yield of tetrasubstituted urea. These conditions include a pH within the range of about 10–13, preferably about 10.5–12.5, maintained by the addition of an alkali metal base, typically sodium hydroxide or potassium hydroxide and especially the former; a reaction temperature of about 40–80° C., preferably about 45–55° C.; and a ratio of equivalents of phosgene to amine in the range of 1.0–1.15:1, preferably about 1.1:1. As used herein, the word "equivalent" designates a number of parts by weight of said compound equal to its molecular weight divided by the number of reactive groups therein under the prevailing reaction conditions. Thus, one equivalent of a secondary amine is equal to its molecular weight and one equivalent of phosgene is half its molecular weight.

Another crucial condition is the proportion of amine with respect to organic solvent, which should be calculated to afford about a 25–90% (by weight), preferably 35–85%, solution of tetrasubstituted urea in the organic solvent, assuming complete conversion has taken place. Suitable proportions of amine can be readily determined by calculation or simple experimentation.

Still another important condition is the volume ratio of organic solvent to water, which should be in the range of about 0.8–5.0:1 and especially about 1.5–4.5:1. Under most circumstances, said ratio will relate inversely to the concentration of calculated product in organic solvent. Thus, at calculated concentrations of 30% and 60% typical volume ratios are 4:1 and 2:1, respectively.

Finally, it is required that the proportion of water be low enough that by-product alkali metal chloride, usually sodium chloride, be present in an amount equal to at least about 95% of the saturation amount for the aqueous system under the prevailing reaction conditions, including temperature. It is practical, and in certain instances perhaps preferred, to maintain saturation or even supersaturation conditions so that at least a portion of the alkali metal chloride generated precipitates out and essentially all amine and product tetrasubstituted urea remain in the organic phase. This simplifies the problem of disposal of waste products, which typically include the aqueous phase when the reaction is complete.

The reaction between the amine and phosgene takes place in two steps, the first being the formation of a substituted carbamoyl chloride and the second the reaction of said carbamoyl chloride with further amine to form tetrasubstituted urea. The reaction is deemed complete when no organically bound chlorine remains in the mixture or the value of organically bound chlorine has reached a minimum. If the described conditions are maintained, yields are typically above 90%.

Following completion of the reaction, it is usually preferred to add water to dissolve any alkali metal chloride which may have precipitated. Then, in step B, water, amine and alkali metal chloride are removed from the first product mixture formed in step A. Since the second reaction forming the Vilsmeier salt proceeds most efficiently under anhydrous conditions, it is preferred to remove substantially all water. Typically, the water content of the anhydrous mixture will be no greater than 50 ppm (by weight).

The major proportion of water and alkali metal chloride may be removed by merely allowing the aqueous and organic phases to separate and removing the aqueous layer. Final traces of water are preferably removed by azeotropic distillation, which is the reason the preferred organic solvents are those which form azeotropic mixtures with water. Any remaining traces of amine will also be removed by the distillation. Often, solid alkali metal chloride will be present in addition to the material dissolved in the aqueous phase, and it may be removed by filtration following the distillation operation.

In step C, the concentration of tetrasubstituted urea in the anhydrous mixture is adjusted to about 40–80% by weight by adding organic solvent or by removal of solvent, typically by distillation. This step is, of course, unnecessary if the tetrasubstituted urea concentration is already within the mandated range.

In step D, phosgene is introduced into the anhydrous mixture at a temperature in the range of about 60–80° C. The ratio of equivalents of phosgene to tetrasubstituted urea when phosgene addition is complete is in the range of about 1.05–1.15:1. The progress of the reaction may be monitored by conventional analytical techniques such as nuclear magnetic resonance spectroscopy, with the mixture being maintained within the 60–80° C. temperature range until the reaction is complete. At that point, unreacted phosgene is removed in step E. "Removal" as defined herein includes removal by reaction, in this step typically by introduction of a quenching proportion of amine, and volatilization as by sparging with nitrogen.

The final reaction, between the Vilsmeier salt and further amine, is conducted in step F. The temperature of this step is typically in the range of about 45–70° C.

Under the preferred conditions where the reaction mixture is anhydrous, the ratio of equivalents of amine to Vilsmeier salt is in excess of 2:1. When the reaction mixture is anhydrous, said ratio is most often in the range of about 2.05–2.5:1. One equivalent of the amine reacts with the Vilsmeier salt to form hexasubstituted guanidine, and another equivalent neutralizes the hydrogen chloride thus generated. If the mixture is not anhydrous, additional phosgene will be required to react with and thus remove any water present.

A convenient means for determining when the Vilsmeier salt has been totally converted to hexasubstituted guanidine is to employ phosgene paper. Unreacted Vilsmeier salt produces a red color upon contact therewith. Thus, the reaction is complete when no such color is produced.

Step G permits isolation of the guanidinium chloride in aqueous solution, said solution also containing alkali metal chloride which is typically present in the amount of about 8–12% by weight, based on total solution. Isolation is achieved by adding an appropriate volume of water in a basic medium, typically at a pH of at least about 13, and removing excess amine, typically by distillation of primarily the organic phase. Following distillation, further water may be added if necessary. The desired guanidinium chloride, being water-soluble, remains in the aqueous phase and the organic phase may be removed and discarded. To maintain the acid-base balance of the resulting aqueous product during employment as a phase transfer catalyst, acid, preferably dilute aqueous mineral acid and typically hydrochloric acid, is finally added to bring the pH of the solution to a value in the range of 2–12, preferably 6–8.

In addition to optimization of the yield of guanidinium chloride, a further advantage of the procedure described hereinabove is that unreacted amine is removed at various stages by distillation. Thus, it may be recovered and recycled.

The second and third aspects of the invention are based on the possible need under certain conditions to stop the process after the preparation of tetrasubstituted urea and/or Vilsmeier salt and store the products. Thus, step A may be isolated and employed separately, as may the combination of steps D and E.

The fourth aspect of the invention is based on three further discoveries. First, guanidinium chlorides having at least three carbon atoms in the chain(s) (whether acyclic or alicyclic) attached to each nitrogen atom (hereinafter sometimes "higher guanidinium chlorides") frequently have reactivity and solubility properties substantially different from those of hexaethylguanidinium chloride. Thus, it is frequently found that the conditions hereinabove described in detail are not necessary or optimal for their preparation. This is particularly true of the concentrations and proportions in steps A–D.

Second, although in the use of the product as a phase transfer catalyst the presence of alkali metal chloride is frequently innocuous, there are circumstances under which it may be detrimental. For example, its presence may require further dilution with water to maintain the solution homogeneous, thus complicating such operations as packaging, handling, shipping and storage. Also, aqueous alkali metal chlorides, especially sodium chloride, are corrosive to equipment made of certain materials such as stainless steel and their presence may therefore be undesirable if such equipment is to be employed. Finally, the presence of alkali metal chlorides in the product formed in the phase transfer catalysis reaction may cause by-products such as sodium nitrite, otherwise marketable for other purposes, to have an excessive chloride ion concentration which prevents them from being saleable. Under circumstances such as these, it may be advantageous to employ a higher guanidinium chloride which is readily separated from alkali metal chloride.

Third, if the proportions of water and organic solvent are suitably adjusted during the concluding operations of the method for preparing higher guanidinium chlorides, the mixture containing the product separates into three phases. The top phase comprises organic solvent and by-products soluble therein. The bottom phase consists essentially of alkali metal chloride brine. The middle phase is essentially free from alkali metal chloride and contains the desired guanidinium chloride, as well as a minor proportion of water.

These findings call forth the fourth aspect, which is a method for preparing higher guanidinium chlorides having steps similar to those of the first aspect but without some of the compositional limitations. It also includes the step of diluting the mixture after formation of the guanidinium salt to cause formation of the aforementioned three phases and separating the middle phase, which comprises said guanidinium salt and water and is substantially free from alkali metal chloride.

The fifth aspect of the invention is directed to the aqueous guanidinium salt solutions obtained according to the first and fourth aspects. The pH of said solutions has been adjusted as previously described.

The sixth aspect is based on the mode of use of the aqueous guanidinium chloride solutions as phase transfer catalysts and its nature is evident from the description hereinafter of the seventh aspect.

That aspect is the use of aqueous solutions of guanidinium chlorides as source materials for the phase transfer catalysts employed in displacement reactions for the formation of polyetherimides and intermediates therefor. As previously mentioned, employment of these guanidinium chlorides in solid form is difficult because they are hygroscopic. However, their conversion to less hygroscopic salts such as bromides requires an additional process step and is thus undesirable for commercial purposes. Thus, it is very advantageous to be able to introduce them as aqueous solutions and subsequently remove water.

In the imide represented by formula I, the A radical generally contains about 6–30 carbon atoms. The imide is generally derived from an o-dicarboxylic acid such as phthalic acid or 2,3-naphthalenedicarboxylic acid; however, derivatives of acids such as 1,8-naphthalenedicarboxylic acid are also suitable. Most preferably, the imide is a phthalimide.

When q is 1, the $R^1$ value is preferably an alkyl and especially a lower alkyl radical (i.e., one containing up to 7 carbon atoms). Most preferably, it is methyl, n-propyl or n-butyl. When q is 2, it is preferably an arylene and especially a phenylene radical, most often m-phenylene, p-phenylene or a mixture thereof.

The bisphenol salts are generally compounds of the formula $$R^2(ZM)_2,\quad(III)$$

wherein $R^2$ is a divalent aromatic radical containing about 6–30 carbon atoms, M is an alkali metal and Z is oxygen or sulfur. The $R^2$ radical may be a hydrocarbon radical or may contain other atoms such as oxygen or sulfur. Illustrative dihydroxyaromatic compounds from which the $R^2$ radicals may be derived are resorcinol, hydroquinone, 4,4'-dihydroxybiphenyl, 4,4'-dihydroxy-3,3',5,5'-tetramethylbiphenyl, bis(4-hydroxyphenyl)methane, 3-hydroxyphenyl-4-hydroxyphenylmethane, 2,2-bis(2-hydroxyphenyl)propane, 2,2-bis(4-hydroxyphenyl)propane (hereinafter "bisphenol A"), 2-(3-hydroxyphenyl)-2-(4-hydroxyphenyl)propane, 1,1-bis(4-hydroxyphenyl)ethane, 2,2-bis(4-hydroxyphenyl)pentane, 1,1-bis(4-hydroxyphenyl)ethylene, 4,4'-dihydroxybenzophenone, bis(4-hydroxyphenyl)ether, bis(4-hydroxyphenyl) sulfide, bis(4-hydroxyphenyl) sulfoxide, bis(4-hydroxyphenyl) sulfone and 3-hydroxyphenyl-4-hydroxyphenyl sulfone.

The preferred $R^2$ radicals are usually

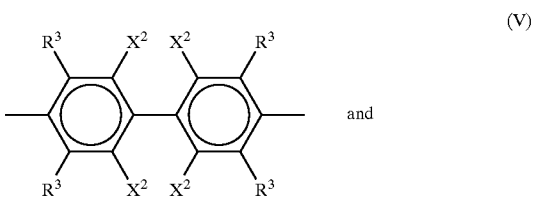

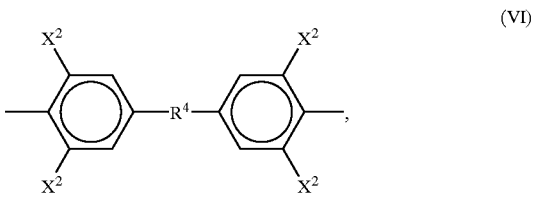

wherein each $R^3$ is independently hydrogen or methyl, $R^4$ is a straight-chain or branched alkylene radical containing 1–5 carbon atoms and each $X^2$ is independently hydrogen or halogen (usually chlorine or bromine). Mixtures of the foregoing formulas are also contemplated. Especially desirable are the bisphenol A salts, having formula VI in which $R^4$ is isopropylidene and each $X^2$ is hydrogen.

The alkali metal in the bisphenol salt may be any of the known alkali metals. Sodium and potassium are usually preferred by reason of availability and low cost, with sodium being especially preferred. The Z value may be oxygen or sulfur and is usually oxygen.

The seventh aspect is applicable in at least two contexts. The first is the displacement reaction of halo- or nitro-substituted phthalimides with alkali metal salts of dihydroxyaromatic compounds (hereinafter sometimes simply "bisphenol salts") in organic solvents of low polarity such as those previously enumerated to produce bis(phthalimido) aromatic compounds; these may be further converted to dianhydrides which undergo reaction with diamines to form polyetherimides. The second is the direct reaction, in similar solvents, of bis(N-substituted phthalimido) compounds having similar substituents, as illustrated by 1,3-bis[(N-(4-chlorophthalimido)]benzene also known as 2,2'-(1,3-phenylene)bis[5-chloro-1H-isoindole-1,3(2H-dione)], with bisphenol salts for the direct formation of the polyetherimides.

It is known that the presence of water in any measurable proportions substantially decreases yield in these reactions. In general, the water content should be below 50 ppm by weight and it is strongly preferred that the reaction mixtures be maintained totally anhydrous. This is most often achieved by combining any reagent which may contain traces of water with an organic solvent which forms an azeotrope with water, as exemplified by the solvents of this type enumerated hereinabove, and removing the water by azeotropic distillation before introducing the other reagent.

The invention permits the guanidinium chloride to be introduced in aqueous solution followed by removal of water from the mixture containing it, typically by azeotropic distillation. In one embodiment, the aqueous solution, with alkali metal chloride present, is azeotropically distilled with toluene or the like prior to introduction of imide and bisphenol salt. In a related embodiment, and provided enough hot toluene is employed to dissolve the guanidinium chloride after distillation of the water (i.e., about 250 ml/g), the toluene solution may be filtered while hot to remove the alkali metal chloride.

For the most part, however, there is no advantage in segregating the phase transfer catalyst from both reagents before removal of the water since a principal advantage of the invention is to introduce it in liquid form. Thus, the often preferred embodiment is the one which also gives rise to the sixth embodiment: water removal is performed on a mixture of phase transfer catalyst with imide and/or bisphenol salt in combination with a solvent such as toluene. When substantially all water has been removed ("substantially" meaning a total water content not greater than 50 ppm by weight), the other reagent may be added and the displacement reaction conducted under conventional conditions. If removal of water can be completed rapidly, the guanidinium chloride may be combined with both reagents. In these embodiments, step P is combined with at least a portion of step R.

In step S, the reaction mixture is normally heated at a temperature in the range of about 100–200° C., preferably about 125–175° C., for product formation. It is preferred to use stoichiometric amounts of the bisphenol salt and imide, but under appropriate conditions an excess of one reagent or the other, generally not more than about 25%, may be employed. An internal standard may be incorporated in the reaction mixture for analytical purposes. The proportion of guanidinium salt is a catalytically effective proportion, most often about 0.1–5.0 mole percent based on imide.

Isolation of the product may be achieved by conventional methods. These typically involve washing with an aqueous alkaline solution followed by drying of the organic phase and solvent stripping.

The invention is illustrated by the following examples.

EXAMPLE 1

A 1-liter, round-bottomed, 5-necked Morton flask was fitted with a mechanical stirrer, pH electrode, thermometer, phosgene dip tube and Claisen head adapter which in turn was fitted with a solid carbon dioxide-acetone condenser and caustic addition port. The flask was charged with 110 g (1.5 moles) of diethylamine, 86 g of toluene and 50 ml of water. Phosgene, 82 g (0.829 mole), was introduced at a rate of 3 g/min with stirring, while the flask was maintained at 50° C. by immersion in a solid carbon dioxide-acetone bath. During the phosgene addition, the pH was maintained at 11.5 by addition of 50% aqueous sodium hydroxide solution as required, by a peristaltic pump connected to a pH-controlled switch.

After phosgene addition was complete, the mixture was heated to 70° C. in an oil bath. Additional caustic was added as required to maintain the pH at 11.5 over a period of about 25 minutes.

After 30 minutes at 70° C., the mixture was cooled to 40° C. and 150 ml of water was added to dissolve salts. The pH was adjusted to 12.0 by the addition of further sodium hydroxide solution. Upon analysis of the mixture, it was found that the yield of tetraethylurea was 93%.

The contents of the flask were transferred to a 1-liter separatory funnel with two 20-ml toluene washes and the aqueous phase was discarded. The toluene solution was returned to the flask and the pH probe and Claisen head were removed and replaced by a stopper and a short path distillation head. The mixture was dried by azeotropic distillation to yield a 62.5% solution of tetraethylurea in toluene. Analysis of the distillate showed the presence of unreacted diethylamine, which could be recycled, and a small amount of tetraethylurea, which could be combined with the principal portion thereof.

The flask was fitted with a pressure-equalizing addition funnel which was charged with 50 ml of diethylamine, thus maintaining the diethylamine in isolation from the phosgene subsequently introduced. The reaction mixture was heated to 80° C. and 76 g (768 mmol) of phosgene was added over 38 minutes, with stirring. Heating was continued for 2.5 hours, after which analysis by nuclear magnetic resonance spectroscopy indicated 99% conversion of tetraethylurea to the Vilsmeier salt.

The reaction mixture was cooled to 50° C. and about 5 ml of diethylamine was added from the addition funnel to quench residual phosgene. Toluene, 193 ml, was added to adjust the Vilsmeier salt concentration to 40%, after which diethylamine to a total of 132 g (2.4 equivalents per equivalent of theoretical tetraethylurea) was added dropwise over about 15 minutes while the temperature was maintained at 55° C. Water, 100 ml, was then added and the flask was again fitted with a pH electrode and Claisen head, the latter in turn being equipped with a caustic addition port and short path distillation head.

Sodium hydroxide solution was added to adjust the pH to 13.3. The mixture was distilled to remove about 255 ml of distillate, after which diethylamine and tetraethylurea could not be detected in the reaction mixture.

Water, 100 ml, was added to dissolve precipitated salts and the mixture was transferred with a 10-ml water wash to a separatory funnel, whereupon it separated into an aqueous and organic phase. The aqueous phase was a solution of the desired hexaethylguanidinium chloride and sodium chloride. The overall yield, based on diethylamine introduced in the first step, was 85.8%.

EXAMPLE 2

The apparatus employed and modified as in Example 1 was charged with 152 g (1.5 moles) of di-n-propylamine, 166 g of toluene and 50 ml of water. Phosgene was added for 27 minutes at 3 g/min, to a total of 81 g (820 mmol), at a temperature of 55° C. and a pH of 11.5 maintained by addition of 50% aqueous sodium hydroxide solution. When phosgene addition was complete, the mixture was maintained at 55° C. for 1 hour with the addition of about 5 ml of di-n-propylamine to quench unreacted phosgene.

The mixture was stirred under nitrogen overnight, after which 100 ml of water was added and the organic layer was separated, washed with two 200-ml portions of 1N hydrochloric acid and two 200-ml portions of water and an aliquot removed for analysis and further use. The yield of tetra-n-propylurea was about 96.5%.

The mixture was returned to the flask and phosgene was introduced at 2 g/min for 40.5 minutes, to a total of 81 g (820 mmol), after which stirring was continued at 80° C. for 2 hours. Unreacted phosgene was sparged from the system with a stream of nitrogen and a further 3.7-g sample was taken for analysis.

Di-n-propylamine, 154.2 g (1.52 moles), was added dropwise at 80° C., with stirring, and the progress of the reaction was monitored with phosgene paper. When amine addition was complete, 100 ml of water was added and the flask was again fitted with a pH electrode. Sodium hydroxide solution was added to raise the pH to 12.0, after which volatiles were removed by distillation. Water and toluene, 100 ml each, were added and azeotropic distillation was continued.

Finally, 100 ml of toluene was added and the mixture was transferred to a separatory funnel. It separated into three phases: a clear bottom aqueous sodium chloride phase, a dark toluene top phase containing organic impurities and a light yellow middle phase containing water and hexa-n-propylguanidinium chloride. The middle phase was separated and the overall yield of guanidinium chloride was determined to be about 76%.

EXAMPLE 3

Following a procedure similar to that of Example 2, a reaction was conducted between 47.9 g (482 mmol) of 4-methylpiperidine and 22.9 g (232 mmol) of phosgene in 962 ml of toluene and 25 ml of water. The Vilsmeier salt was formed by the addition of 22 g (220 mmol) of phosgene. Finally, conversion to tris(4-methylpiperidinyl)guanidinium chloride was achieved by reaction with 25.1 g (251 mmol) of 4-methylpiperidine. The overall yield was 73%.

EXAMPLE 4

A 2-liter, 5-necked oil-jacketed glass vessel equipped with a mechanical stirrer, nitrogen inlet means and a Dean-Stark trap topped with a reflux condenser was charged in a nitrogen atmosphere with 335 g (1.63 moles) of 4-nitro-N-methylphthalimide, 1400 g of toluene and 6.2 g of an aqueous solution similar to the product of Example 1 and consisting of 34.4% hexaethylguanidinium chloride, 10% sodium chloride and 55.6% water (i.e., 8 mmol of hexaethylguanidinium chloride). The solution was heated to reflux and the water was removed by azeotropic distillation of about 400 g of toluene. The resulting solution was added via a flexible fitting to a similarly equipped 5-liter glass vessel which had been charged with a mixture of 222 g (815 mmol) of bisphenol A disodium salt and 700 g of toluene. The reaction mixture was maintained at 120° C. for 60 minutes, after which analysis by high pressure liquid chromatography showed that the reaction was complete and that the yield of 2,2-bis[4-(3,4-carboxyphenoxy)phenyl]propane bis-N-methylimide was 99.4%.

The mixture was cooled to 80° C. and washed at this temperature with three 580-ml portions of 1% aqueous sodium hydroxide solution. The purified bisimide solution had a yellowness index of 2.0.

EXAMPLE 5

A 40,000-liter steam-jacketed vessel was charged in a nitrogen atmosphere with 4,276 kg (20.8 kg-moles) of 4-nitro-N-methylphthalimide and 15,649 kg of toluene. The mixture was heated to about 115° C., with stirring, and 68.1 l of an aqueous solution similar to the product of Example 1 and comprising 28.6% hexaethylguanidinium chloride and about 10% sodium chloride (0.08 kg-mole of hexaethylguanidinium chloride) was added over 10 minutes with water being continuously removed by azeotropic distillation. Distillation was continued until about 4,100 kg of toluene had been removed, at which point the reaction temperature was about 119° C. A suspension of about 2,812 kg (10.33 kg-moles) of bisphenol A disodium salt in about 7,710 kg of toluene was added, whereupon an exothermic reaction occurred resulting in a 3° temperature increase. The stoichiometry of the mixture was adjusted to 2:1 by addition of 4-nitro-N-methylphthalimide and the reaction was continued until it was complete as shown by high pressure liquid chromatography. Workup was conducted as in Example 4 to yield the desired 2,2-bis[4-(3,4-carboxyphenoxy)phenyl] propane bis-N-methylimide in toluene solution.

EXAMPLE 6

A mixture of 2.152 grams (7.9 mmol) of bisphenol A disodium salt in 50 ml of o-dichlorobenzene is heated to 200° C. under nitrogen and 3.455 g (7.9 mmol) of 1.3-bis [N-(4-chlorophthalimido)]benzene is added in admixture with 10 ml of o-dichlorobenzene. Distillation is initiated and 1 0 ml of o-dichlorobenzene is removed, after which 0.55 g of an aqueous solution similar to the product of Example 1 and comprising 35% hexaethylguanidinium chloride is added dropwise at a rate such that the water vapor is swept out by a nitrogen stream without foaming. The mixture is stirred for 5 hours at 200° C., whereupon gel permeation chromatographic analysis shows that the resulting polyetherimide has a weight average molecular weight of about 40,000 relative to polystyrene.

What is claimed is:

1. A method for preparing a polyetherimide or intermediate thereof which comprises the steps of:

(P) removing substantially all water from a mixture comprising: an organic solvent of low polarity; an imide having the formula

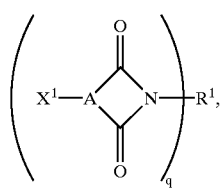

(I)

wherein A is a trivalent aromatic radical, $R^1$ is an unsubstituted or substituted mono- or divalent hydrocarbon radical containing about 1–13 carbon atoms, $X^1$ is halo or nitro and q is 1 or 2; an aqueous solution of a hexasubstituted guanidinium chloride and optionally an alkali metal chloride to form an anhydrous mixture comprising said hexasubstituted guanidinium chloride, said organic solvent and said imide; wherein said mixture comprises not greater than about 50 ppm by weight water;

(R) preparing, in an organic solvent of low polarity, an anhydrous mixture comprising said hexasubstituted guanidinium chloride; an alkali metal salt of a dihydroxyaromatic compound; said imide; and optionally an alkali metal chloride; and (S) effecting reaction in said anhydrous mixture between said alkali metal salt and said imide.

2. A method according to claim 1 wherein the guanidinium chloride is hexaethylguanidinium chloride.

3. A method according to claim 1 wherein said aqueous guanidinium chloride solution is substantially free from alkali metal chloride.

4. A method according to claim 3 wherein the guanidinium chloride is tris(4-methylpiperidinyl)guanidinium chloride.

5. A method according to claim 1 wherein the alkali metal salt is the disodium salt of bisphenol A.

6. A method according to claim 5 wherein $X^1$ is nitro, A is the radical derived from benzene, $R^1$ is methyl and q is 1.

7. A method according to claim 1 wherein $X^1$ is chloro, A is the radical derived from benzene, $R^1$ is p-phenylene, m-phenylene or a mixture thereof and q is 2.

8. A method according to claim 1 wherein the mixture of step P further comprises said alkali metal salt.

9. A method according to claim 1 wherein said organic solvent comprises a solvent which forms an azeotrope with water.

10. A method according to claim 1 wherein said aqueous guanidinium chloride solution comprises alkali metal chloride.

11. A method according to claim 9 wherein the alkali metal chloride is sodium chloride.

12. A method for preparing a polyetherimide or intermediate thereof which comprises the steps of:

(P) removing substantially all water from a mixture comprising: an organic solvent of low polarity; an imide having the formula

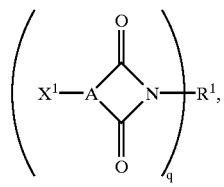

(I)

wherein $X^1$ is chloro, A is a radical derived from benzene, $R^1$ is p-phenylene, m-phenylene or a mixture thereof and q is 2; an aqueous solution of hexaethyl guanidinium chloride and sodium chloride to form an anhydrous mixture comprising said guanidinium chloride, said organic solvent and said imide; wherein said mixture comprises not greater than about 50 ppm by weight water;

(R) preparing, in an organic solvent of low polarity, an anhydrous mixture comprising said guanidinium chloride and sodium chloride; bisphenol A disodium salt; and said imide; and (S) effecting reaction in said anhydrous mixture between said disodium salt and said imide.

13. A method for preparing a polyetherimide or intermediate thereof which comprises the steps of:

(T) preparing a mixture comprising: an organic solvent of low polarity; an imide having the formula

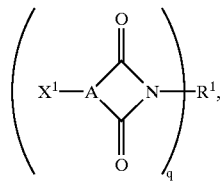

(I)

wherein A is a trivalent aromatic radical, $R^1$ is an unsubstituted or substituted mono- or divalent hydrocarbon radical containing about 1–13 carbon atoms, $X^1$ is halo or nitro and q is 1 or 2; and an alkali metal salt of a dihydroxyaromatic compound;

(U) adding to the heated mixture from step (T) an aqueous solution comprising a hexasubstituted guanidinium chloride and optionally an alkali metal chloride, at such a rate of addition that water is removed as the solution is added; and (V) effecting reaction in said mixture between said alkali metal salt and said imide.

14. A method according to claim 13 wherein the guanidinium chloride is hexaethylguanidinium chloride.

15. A method according to claim 13 wherein said aqueous guanidinium chloride solution comprises alkali metal chloride.

16. A method according to claim 15 wherein the alkali metal chloride is sodium chloride.

17. A method according to claim 13 wherein said aqueous guanidinium chloride solution is substantially free from alkali metal chloride.

18. A method according to claim 13 wherein the guanidinium chloride is tris(4-methylpiperidinyl)guanidinium chloride.

19. A method according to claim 13 wherein the alkali metal salt is the disodium salt of bisphenol A.

20. A method according to claim 13 wherein $X^1$ is nitro, A is a radical derived from benzene, $R^1$ is methyl and q is 1.

21. A method according to claim wherein $X^1$ is chloro, A is a radical derived from benzene, $R^1$ is p-phenylene, m-phenylene or a mixture thereof and q is 2.

22. A method for preparing a polyetherimide or intermediate thereof which comprises the steps of:

(T) preparing a mixture comprising: an organic solvent of low polarity; an imide having the formula

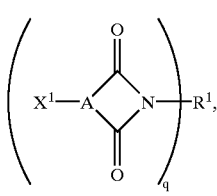

(I)

wherein $X^1$ is chloro, A is a radical derived from benzene, $R^1$ is p-phenylene, m-phenylene or a mixture thereof and q is 2; and bisphenol A disodium salt;

(U) adding to the heated mixture from step (T) an aqueous solution comprising a hexaethyl guanidinium chloride and sodium chloride, at such a rate of addition that water is removed as the solution is added; and (V) effecting reaction in said mixture between said disodium salt and said imide.

* * * * *